United States Patent [19]

Spielmann et al.

[11] 4,339,594

[45] Jul. 13, 1982

[54] PROCESS FOR THE MANUFACTURE OF PHENYLACETIC ACID AND SIMPLE DERIVATIVES THEREOF

[75] Inventors: Werner Spielmann, Kelkheim; Georg Schaeffer, Hofheim am Taunus, both of Fed. Rep. of Germany

[73] Assignee: Hoechst Aktiengesellschaft, Frankfurt am Main, Fed. Rep. of Germany

[21] Appl. No.: 202,605

[22] Filed: Oct. 31, 1980

[30] Foreign Application Priority Data

Nov. 3, 1979 [DE] Fed. Rep. of Germany ....... 2944480

[51] Int. Cl.$^3$ ............................................. C07C 69/76
[52] U.S. Cl. ..................................... 562/465; 560/19; 560/37; 560/55; 560/81; 560/105; 560/75; 562/442; 562/455; 562/478; 562/480; 562/489; 562/493

[58] Field of Search ............... 562/478, 442, 455, 465, 562/478, 480, 489, 493; 560/75, 19, 37, 55, 81, 105

[56] References Cited

U.S. PATENT DOCUMENTS 4,198,526 4/1980 Edwards ............................ 562/478

FOREIGN PATENT DOCUMENTS

| 3825 | 9/1979 | European Pat. Off. ........... | 562/478 |
| 2445311 | 8/1980 | France ................................ | 562/478 |
| 50-92344 | 7/1980 | Japan .................................. | 562/478 |

*Primary Examiner*—Paul J. Killos
*Attorney, Agent, or Firm*—Curtis, Morris & Safford

[57] ABSTRACT

Phenylacetic acid and the simple derivatives thereof are prepared by catalytic hydrogenation of mandelic acid and its appropriate derivatives in the presence of a noble metal catalyst in aqueous solution which is free from mineral acid, especially free from hydrochloric acid.

6 Claims, No Drawings

PROCESS FOR THE MANUFACTURE OF PHENYLACETIC ACID AND SIMPLE DERIVATIVES THEREOF

Phenylacetic acid and its simple derivatives, such as, for example o-, m- and p-hydroxy, -alkoxy and -halogeno-phenylacetic acids and the salts and esters thereof are valuable intermediates and in part also final products in various fields, especially in the pharmaceutical field. 3-Fluoro-4-hydroxy-phenylacetic acid, for example, has a thyreostatic effect and 3-chloro-4-(prop-2-enyloxy)-phenylacetic acid has an antipyretic effect. 4-(2'-hydroxy-3'-isopropylamino-propoxy)-phenylacetamide is known as β-receptor blocker.

Different methods are known for the manufacture of phenylacetic acid. One usual method for the manufacture of (unsubstituted) phenylacetic acid uses toluene as starting material which is chlorinated to give benzyl chloride. The benzyl cyanide obtained therefrom by reaction with sodium cyanide is then saponified to give phenylacetic acid.

Another frequently used method comprises the reduction of mandelic acid with potassium iodide, red phosphorus and phosphoric acid. Yields of up to 90% of the theory are indicated (Fieser & Fieser, Lehrbuch der organischen Chemie, Verlag Chemie GmbH, Weinheim/Bergstrasse, Federal Republic of Germany, pages 784/785 (1960)).

The two methods, especially when they are carried out on an industrial scale, involve numerous problems such as the handling of NaCN which is unpleasant and the use of KI or HI which is expensive.

Attempts have also been made to reduce mandelic acid and some derivatives thereof (o-chloro-, o-hydroxy-, p-methoxy-mandelic acid) catalytically with hydrogen in contact with a Pd/BaSO$_4$ catalyst to the corresponding phenylacetic acids. At first the reduction was successful only with the corresponding O-acyl-mandelic acids, that is to say after acylation of the aliphatic OH group (cf. Rosenmund and Schindler, Arch. Pharm. 266, page 281 (1928)). The reduction was carried out in xylene, cumene and tetralin as solvent at temperatures above 200° C. and the yields did not exceed 60% of the theory. Mandelic acids which had not been O-acylated were not hydrogenated under these conditions.

Later on the catalytic hydrogenation of mandelic acid and of some of its derivatives to give the corresponding phenylacetic acids has been successful also without previous O-acylation at room temperature in glacial acetic acid by adding to the glacial acetic acid definite acid substances (HBr, ZnCl$_2$/HCl, H$_2$SO$_4$, HClO$_4$) (cf. Weidlich, Meyer-Delius, Berichte der Deutschen Chemischen Gesellschaft 73, pages 325 to 327 (1940); Kindler et al., Liebigs Annalen 545, pages 9 to 15 (1943)). Yields of up to about 90% of the theoretical of phenylacetic acid and phenylacetic acid derivatives are indicated. It is mainly the formation of certain molecular compounds of mandelic acid (derivatives) with the acid additives added to the glacial acetic acid as well as a partial esterification of the alcoholic OH group, causing a certain "activation" of said alcoholic OH group that are made responsible for the success of the reaction under the indicated, relatively mild conditions (at higher temperatures the degree of hydrogenation at the nucleus is increased). This activation and the corresponding desired hydrogenation result (i.e., yield of phenylacetic acid and its derivatives) decreases as the conditions for the existence of said molecule compounds and esters becomes more unfavorable. It is said that such unfavorable conditions are caused, for example, by the presence of water (Liebigs Annalen 545, page 10 (1943)).

It has also been proposed to carry out the catalytic hydrogenation of mandelic acid to give phenylacetic acid in a good yield even in aqueous solution-however not in a pure aqueous solution but in aqueous mineral acid, in particular aqueous hydrochloric acid (BE-PS 867 289). With the use of a Pd catalyst (on carbon as carrier material) the yield of phenylacetic acid is said to be 85% of the theoretical. It is quite possible that in this case, too, the reaction takes place via an "activated" mandelic acid (by the mineral acid). An undesired hydrogenation at the nucleus is said to be avoided by the presence of chlorine ions.

It is a drawback of the known processes for the manufacture of phenylacetic acid (derivatives) by catalytic hydrogenation of mandelic acid (derivatives) that the mandelic acid (derivatives) have to be "activated" to a greater or lesser extent. This involves additional synthesis stages (O-acylation), expensive working up, considerable waste water pollution and corrosion problems (glacial acetic acid/inorganic acids or salts, aqueous mineral acids as solvent).

Because of the otherwise favorable synthesis of phenylacetic acid and phenylacetic acid derivatives by catalytic hydrogenation of mandelic acid and corresponding derivatives thereof, it has, therefore, been desirable to improve the known catalytic reduction processes.

This objective could be achieved according to the invention by carrying out the catalytic hydrogenation in an aqueous solution free from mineral acid, in particular hydrochloric acid.

It is, therefore, the object of the present invention to provide a process for the manufacture of phenylacetic acid and of its simple derivatives by catalytic hydrogenation of mandelic acid and the corresponding derivatives thereof in the presence of a noble metal catalyst in aqueous solution, wherein the aqueous solution is free from mineral acid, especially free from hydrochloric acid. Knowing the state of the art, it has been extremely surprising that the catalytic hydrogenation of mandelic acid (derivatives) to give phenylacetic acid (derivatives) takes place in aqueous solution without addition of special additives, that is to say without "activation" of the mandelic acid, in practically the same manner and with practically the same yields as obtained by the known hydrogenation of "activated" mandelic acid. According to the aforesaid state of the art it could rather be expected that without a special "activation" of the mandelic acid (derivatives) any reduction to phenylacetic (derivatives) would not take place in an acceptable manner. It has also been surprising that in the process of the invention a noticeable hydrogenation at the nucleus does not take place in the absence of chlorine ions, as the above Belgian Pat. No. 867,289 expressly states that the presence of chlorine ions is necessary to avoid an (undesired) hydrogenation at the nucleus.

Suitable starting materials in the process of the invention are mandelic acid and all possible derivatives thereof mono- or polysubstituted at the nucleus (by substituents substantially inert under the reduction conditions), as well as the salts and esters thereof. Preferred starting products are compounds of the following formula

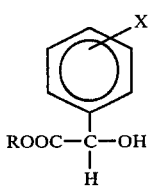

in which
X denotes OH, alkoxy, preferably $C_1$–$C_4$alkoxy, aryloxy, preferably phenoxy, alkyl, preferably $C_1$–$C_4$alkyl, halogen, preferably F, $CF_3$, $COOR^1$ with $R^1$ being alkyl, preferably $C_1$–$C_4$alkyl, $CONR^2R^3$ with $R^2$ and $R^3$ being H, alkyl, preferably $C_1$–$C_4$alkyl, $NR^2R^3$ with $R^2$ and $R^3$ being H, alkyl, preferably $C_1$–$C_4$alkyl, R denotes H, M (a metal cation, preferably an alkali metal or $NH_4$ cation, more preferably $Na^+$), alkyl, preferably $C_1$–$C_4$alkyl, or aryl, preferably $C_6H_5$.

More specific starting compounds, i.e. those which do not fall under the formula of preferred starting compounds as well as those which correspond to said formula are, for example:
3-fluoro-4-hydroxymandelic acid
4-hydroxy-3-ethoxymandelic acid
3-carboxy-4-hydroxymandelic acid
p-hydroxymandelic acid
p-hydroxymandelic acid ethyl ester
p-methoxymandelic acid
o-methoxymandelic acid
p-tert.butylmandelic acid
p-carbethoxymandelic acid ethyl ester.

Especially preferred starting compounds are m- and p-hydroxy- and m- and p-alkoxy-(preferably $C_1$–$C_4$alkoxy)mandelic acid, above all the former (m- and p-hydroxymandelic acid) and the sodium salts thereof.

Suitable noble metal catalysts to be used in the process of the invention are practically all those known for splitting benzyl-O linkages (cf. Organic Reactions, volume VII, chapter 5, pages 264 et seq. (1953)). More particularly, suitable hydrogenation catalysts are the metals of the 8th subgroup of the Periodic Table of the elements (Ru, Rh, Pd, Os, Ir, Pt), palladium being preferred. The metal catalyst is usually applied onto a known carrier material such as, for example, $SiO_2$, carbon, aluminum oxide, aluminum silicates, $BaSO_4$, and the like, preferably $BaSO_4$ or $SiO_2$. The concentration of the metal on the carrier material can be varied within wide limits, it is preferably in the range of from about 1 to 5% by weight. In principle, the catalyst amount can be varied within wide limits also with respect to the starting compound used, preferably the metal amount is in the range of from about 0.01 to 0.5% by weight.

The characteristic feature of the process of the invention is the fact that the catalytic hydrogenation of mandelic acid or its respective derivatives is carried out in an aqueous solution that is free from mineral acid, especially from hydrochloric acid. At least 50% by weight of the solution should be water. If the solvent does not consist of water alone, there can be used additionally mainly low boiling alcohols, preferably $C_1$–$C_4$alcohols such as methanol, ethanol, n- and i-propanol (of the butanols practically only n- and i-butanol) and optionally, up to about 10%, calculated on the total solution, of other organic dissolving intermediaries such as, for example, acetic acid, dioxane and the like. The alcohols and other organic dissolving intermediaries mentioned can be used individually or in the form of mixtures of any two or more thereof. The preferred solvent in the process of the invention is, however, water.

As it is usual in catalytic reductions in solution, the concentration of the starting product in the solvent can practically be chosen as desired. There should only be taken into consideration the dissolution conditions and economical aspects (very dilute solutions are uneconomical).

The reduction can be carried out at temperatures practically from room temperature to about 200° C., preferably, however, in the range of from about 50° to about 200° C., more preferably about 90° to 150° C.

The reaction takes place at atmospheric pressure as well as under a hydrogen excess pressure of up to about 20 bar, preferably up to about 8 bar. In general, higher pressures do not offer any advantage.

When the reaction is carried out without hydrogen excess pressure, it proved advantageous to pass hydrogen through the mixture, which is thoroughly stirred at room temperature, and to recycle the hydrogen in excess into the reaction vessel.

When operating under a hydrogen excess pressure, the hydrogenation is carried out in an autoclave previously gassed with hydrogen.

According to a preferred embodiment of the process of the invention the starting product is added in dosed quantities to the solvent containing the catalyst, this is valid for the hydrogenation without and with hydrogen excess pressure.

The reaction time depends on the reaction conditions (pressure, temperature, concentrations), in general it is in the range of from about 2 to 30 hours.

In the process of the invention mandelic acid is converted into phenylacetic acid and mandelic acid derivatives yield the corresponding phenylacetic acid derivatives. The final products are worked up and isolated in the manner usual for mixtures of catalytic hydrogenations. According to a suitable method for working up the catalyst is separated from the hot reaction mixture by filtration and the filtrate is concentrated by evaporation if desired. When cooling to room temperature, the reaction product usually separates in crystal form and it is then filtered off.

The yields of phenylacetic acid and of the respective derivatives are in the same order of magnitude as the yields of the known catalytic reduction of mandelic acid (derivatives) (up to about 90% of the theoretical). The high yields and the fact that no "activating" additives need be used in the process of the invention, whereby waste water, corrosion and other problems of the known processes are eliminated, constitute a considerable progress of the art.

The following examples illustrate the invention.

EXAMPLE 1

0.5 g of $Pd/BaSO_4$ (1% impregnation) is suspended in a solution of 20 g of p-hydroxymandelic acid hydrate or the corresponding amount of anhydrous acid in 100 ml of water. The mixture is heated to 90° C. internal temperature while vigorously stirring and passing through a $H_2$ current of approximately 100 l/hr. The steam entrained by the gas is condensed and recycled into the reaction vessel.

After 20 hours the conversion is found to be about 80%, verified by thin layer chromatography.

The catalyst is separated by filtering the hot solution and the cold filtrate is extracted with ether to separate the p-hydroxyphenylacetic acid formed from unreacted p-hydroxymandelic acid. After concentration by evaporation of the ether solution, 12.0 g (75% of the theoretical) of p-hydroxyphenylacetic acid are obtained.

EXAMPLE 2

In an autoclave with stirrer a mixture of 20 g of p-hydroxymandelic acid hydrate, 50 ml of water and 0.5 g of catalyst (1% Pd/BaSO$_4$) is hydrogenated at 150° C. for 3 hours under a H$_2$ partial pressure of 5 bar. The hot reaction mixture is then filtered to separate the catalyst and the filtrate is left to stand over-night at room temperature. The main quantity of p-hydroxyphenylacetic acid separates in crystal form. Further concentration of the mother liquor yields an additional amount of reaction product. Total yield 12.8 g of 80% of the theoretical.

This example is repeated under identical conditions with other catalysts. The results are listed below.

| catalyst | yield |
| --- | --- |
| 1 g 0.5% Pd/SiO$_2$ | 12.4 g = 72% of the theoretical |
| 0.1 g 5% Pt/C | 9.2 g = 57% of the theoretical |

EXAMPLE 3

In an autoclave with stirrer a suspension of 0.5 g of Pd/BaSO$_4$ (1% impregnation) in 50 ml of water is heated to 150° C. under a partial pressure of H$_2$ of 5 bar and a solution of 20 g of p-hydroxymandelic acid hydrate in 50 ml of water is pumped in over a period of 2 hours. Hydrogenation is continued for 2 hours, the hot solution is filtered to separate the catalyst and the filtrate is concentrated to about 60 ml. On cooling to room temperature the main quantity of p-hydroxyphenylacetic acid crystallizes over-night. A further amount thereof is obtained by concentration of the mother liquor. Total yield 13.6 g or 85% of the theoretical.

EXAMPLE 4

In an autoclave with stirrer 50 g of the sodium salt of p-hydroxymandelic acid hydrate and 5 g of 5% Pd/BaSO$_3$ in 300 ml of water are heated to 115° C. under a H$_2$ pressure of 5 bar and the mixture is hydrogenated for 10 hours at 115° C. The reaction solution obtained is filtered to separate the catalyst and acidified to pH 2 with concentrated hydrochloric acid. The aqueous solution is extracted four times, each time with 80 ml of diethyl ether, the combined ether phases are dried over Na$_2$SO$_4$ and evaporated to dryness. 18.6 g of p-hydroxyphenylacetic acid (85% of the theoretical, calculated on reacted sodium salt of p-hydroxymandelic acid hydrate) are obtained.

Unreacted p-hydroxymandelic acid can be recovered from the aqueous phase in the form of its sodium salt. To this end the pH of the mixture is adjusted to 6.5 with 2 N NaOH and the mixture is evaporated to a small volume. About 20 g of sodium salt of p-hydroxymandelic acid hydrate crystallize from the residue obtained.

What is claimed is:

1. A process for the manufacture of phenylacetic acid or a derivative thereof consisting essentially of catalytically hydrogenating mandelic acid or a corresponding derivative thereof in the presence of a noble metal catalyst in an aqueous solution free of any mineral acid, said catalytic hydrogenation being conducted at a temperature ranging from room temperature to about 200° C. and at a pressure ranging from atmospheric to about 20 bar hydrogen pressure.

2. The process of claim 1, wherein the temperature is in the range of about 90° C. to about 150° C.

3. The process of claim 1, wherein the mandelic acid or derivative thereof is a compound having the formula

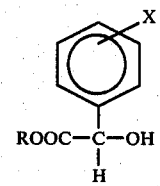

wherein
X is OH, alkoxy, preferably C$_1$-C$_4$ alkoxy, aryloxy, preferably phenoxy, alkyl, preferably C$_1$-C$_4$ alkyl, halogen, preferably F, CF$_3$, COOR$^1$ with R$^1$ being alkyl, preferably C$_1$-C$_4$-alkyl, CONR$^2$R$^3$ with R$^2$ and R$^3$ being H, alkyl, preferably C$_1$-C$_4$ alkyl, NR$^2$R$^3$ with R$^2$ and R$^3$ being H, alkyl, preferably C$_1$-C$_4$ alkyl,
R is H, M (a metal cation, preferably an alkali metal or
NH$_4$ cation, more preferably Na$^+$), alkyl, preferably C$_1$-C$_4$ alkyl, or aryl, preferably C$_6$H$_5$.

4. The process of claim 3, wherein the compound is m- or p-hydroxymandelic acid or m- or p-alkoxymandelic acid or sodium salts thereof.

5. The process of claim 1, 3 or 4, wherein the catalyst is palladium on a barium sulfate or SiO$_2$ carrier.

6. The process of claim 1, 3 or 4, wherein the mandelic acid or derivative thereof is added to the aqueous solvent containing the catalyst during hydrogenation.

* * * * *